United States Patent [19]

Fernandez et al.

[11] Patent Number: 4,990,702
[45] Date of Patent: Feb. 5, 1991

[54] HALOGEN EXCHANGE FLUORINATION

[75] Inventors: Richard E. Fernandez, Bear; Wendel R. Cassel, Newark, both of Del.; Frederick W. Mader, Kennett Square, Pa.

[73] Assignee: E. I. Du Pont de Nemours and Company, Wilmington, Del.

[21] Appl. No.: 480,605

[22] Filed: Feb. 15, 1990

[51] Int. Cl.$^5$ .............................................. C07C 17/20
[52] U.S. Cl. ................................................... 570/170
[58] Field of Search .......................................... 570/170

[56] References Cited

U.S. PATENT DOCUMENTS 4,311,863  1/1982  Gumprecht ........................ 570/170

Primary Examiner—Alan Siegel

[57] ABSTRACT

A process for halogen exchange fluorination by contacting a halocarbon having a replaceable halogen other than fluorine with CsF or RbF·nHF wherein n is 0.5–3 to provide a fluorinated hydrocarbon having at least one more fluorine than the starting halocarbon and, optionally, regenerating the MF·nHF with additional HF, or in a continuous process, with excess HF in the feed.

14 Claims, No Drawings

HALOGEN EXCHANGE FLUORINATION

FIELD OF INVENTION

This invention relates to the halogen exchange fluorination of saturated halocarbons to the corresponding halocarbon having at least one additional fluorine-substitution than the original halocarbon. More particularly, the invention relates to the conversion of a saturated halocarbon having at least one chlorine or bromine substitution to the corresponding halocarbon having at least one fluorine substitution replacing the "at least one chlorine or bromine substitution." Of greatest interest is the invented process for improving the conversion of 2-chloro- or 2-bromo-1,1,1-trifluorethane, $CF_3CH_2Cl$ or $CF_3CH_2Br$, hereinafter referred to as "HCFC-133a" and "HBFC-133aB1" respectively, to 1,1,1,2-tetra-fluoroethane, $CF_3CH_2F$, hereinafter referred to as "HFC-134" and, optionally, recovering the resulting metal chloride or bromide as the metal fluoride for recycling into the conversion process.

BACKGROUND OF THE INVENTION

HFC-134a and its isomer, 1,1,2,2-tetrafluoroethane, $CHF_2$–$CHF_2$, hereinafter referred to as "HFC-134", are potentially useful as aerosol propellants and as refrigerants. They are of particular interest as replacements for Freon ® 12, the commercial refrigerant currently used in substantially all automotive air conditioning systems.

Heretofore, however, the production of HFC-134 and HFC-134a has not been commercially attractive. In particular, a definite need exists for converting HCFC-133a to HFC-134a by a process that is readily adaptable to continuous operation, that minimizes the need for hydrogen fluoride as a fluorine source, that provides the desired tetrafluoro compound at high conversion and selectivity levels and that provides the desired compound in a high state of purity.

PRIOR ART

As stated in U.S. Pat. No. 4,311,863, (column 1, lines 26 ff.) "It is apparent from the prior art that the chlorine atom of the —$CH_2Cl$ group (as in CFC-133a) is highly resistant to halogen exchange with HF." As "prior art," the inventor in this patent discloses the following references: U.S. Pat. No. 2,885,427; U.S. Pat. No. 3,664,545; U.S. Pat. No. 4,129,603; and in a book by Hudlicky p. 93 of "Chemistry of Organic Fluorine Compounds", Mac-Millan Co., New York, N.Y. (1962).

U.S. Pat. No. 2,885,427 discloses the preparation of HFC-134a by the vapor phase reaction of trichloroethylene with HF in the presence of a catalyst prepared by heating hydrated chromium fluoride in the presence of oxygen. The resultant product is a mixture of fluorocarbons in which HFC-134a is reported as being present in an amount of 3 mol %.

Hudlicky in his book and U.S. Pat. No. 3,644,545 disclose the difficulty of fluorine exchange on —$CH_2Cl$ groups with HF in an antimony-catalyzed liquid phase reaction and in a vapor phase reaction, respectively.

U.S. Pat. No. 4,129,603 discloses the vapor phase reaction of CFC-133a with HF in the presence of chromium oxide catalyst to produce a fluorocarbon mixture in which the HFC-134a is reported as 18.2% by volume.

U.S. Pat. No. 1,914,135; Australian Pat. No. 3,141; U.S. Pat. No. 2,739,989: and U.S. Pat. No. 3,843,546 disclose halogen exchange fluorination using alkali metal or alkaline earth metal fluorides. However, these metal fluorides have relatively low orders of reactivity; and processes involving them are generally best conducted in the vapor phase at elevated temperature of 350° to 550° C. by passing the gaseous halocarbon over or through a bed of the solid metal fluoride. The metal halide by-product tends to coat the metal fluoride as reaction progresses so that the reaction rate is retarded; frequent changes of metal fluoride are necessitated; and other expedients, as set forth in these patents, must be imposed to ameliorate the problem.

British Pat. No. 941,144 discloses that the elevated temperatures required in the gas-solid processes can be reduced and the yields improved by employing a gas-liquid process. A gaseous chlorocarbon is passed through a metal fluoride-metal chloride melt at a temperature of about 300° to 375° C. The metal fluorides disclosed are, inter alia, sodium, potassium and calcium fluorides. The molten metal chloride which functions as a solvent for the fluoride may be ferric or zinc chloride or mixtures thereof or these mixtures with sodium chloride.

U.S. Pat. No. 4,311,863 discloses a gas-liquid halogen exchange process in an aqueous medium. Specifically, the process involves converting HCFC-133a to HFC-134a by reaction with potassium, cesium or rubidium fluoride in a 25 to 65 weight % aqueous solution at about 200° to 300° C. under autogenous pressure. Although the process can provide adequate yields of HFC-134a, it is not readily adaptable to low cost, economic, continuous operation, particularly in view of the higher pressures required to maintain the aqueous mixture in the liquid state at the operating temperatures required. It should be noted that at column 5, line 34 ff. of this patent, it is disclosed that "HF in the absence of water does not further the reaction. . . . 2-chloro-1,1,1-trifluoroethane (CFC-133a) was contacted with fused KF.HF with no water present. No <u>reactionoccurred</u>." (Underline added).

SUMMARY OF INVENTION

The present invention is a process for the halogen exchange fluorination of a saturated halocarbon, preferably a continuous process, comprising the following steps:

1. Intimately contacting a halocarbon having at least one replaceable halogen other than fluorine, i.e., chlorine or bromine, in the molecule with an anhydrous molten composition containing at least 50 mole % of a compound or compounds having the formula MF.nHF wherein "M" is at least one of Cesium, Cs, or Rubidium, Rb, preferably Cs, and "n" is a number from about 0.5 to 3, preferably about 0.5 to 1, at a temperature of about 30° C. to just below the lower of the decomposition temperature of the original halocarbon or that of the fluorinated product, preferably about 200° C. to about 350° C., at a subatmospheric or superatmospheric pressure as high as 2000 psi, preferably the latter for increased productivity, usually 14.7 psi to about 1500 psi, for a period of a few seconds to several hours, usually 0.5 minute to two hours, i.e., a pressure and time sufficient to provide at least one reaction product having at least one more fluorine atom in the molecule than the original halocarbon and a residual molten composition at least partially depleted in fluoride content and enriched in its other-than-fluoride halide content;

2. Isolating and recovering the fluorinated reaction product from the residual molten composition; and, optionally, 3. Contacting the residual composition with anhydrous HF in the presence or absence of the halocarbon to convert the other-than-fluoride halide content to HX wherein X is chlorine or bromine, and separating the gaseous HX from the molten composition.

The process of this invention, particularly when HCFC-133a is the saturated halocarbon, is to intimately contact HCFC-133a with molten $C_sF \cdot HF$ at a temperature of 180° C. to 350° C. to produce HFC-134a in high conversions, high yields and in a high state of purity without any substantial amount of objectionable unsaturated by-products. Optionally, the cesium chloride produced in the conversion may be treated with additional HF to regenerate cesium fluoride accompanied by the production of gaseous HCl which is removed from the operation. The cesium fluoride is recycled with HF to form $CsF \cdot n\ HF$, which in turn serves to convert additional HCFC-133a to HFC-134a.

In the preferred continuous process, the fluorinatable saturated halohydrocarbon is cofed with HF into a continuous feed stirred tank reactor, known in the art as a "CFSTR", the amount of HF being sufficient to carry out the fluorination of the saturated halocarbon and the regeneration of the $MF \cdot nHF$ from the metal halide formed during fluorination continuously and simultaneously.

Specifically where HCFC-133a is the saturated halocarbon and $CsF \cdot HF$ is used, HCFC-133a is cofed with HF into the molten composition containing at least 50 mole % of CSF HF at a temperature of 180° C. to 350° C. to produce HFC-134a and, with the excess HF, simultaneously convert CsCl (Formed along with HFC-134a as shown in equation (2) below) to CsF with the continuous release of HCl. The HFC-134a is isolated and further purified, if necessary, before being stored for intimate sale as a refrigerant or otherwise.

The following equations depict the theory of operation of this invention:

(1) $CsF \cdot nHF \rightarrow CsF + nHF$ 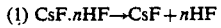

(2) $CsF + 133a \rightarrow 134a + CsCl$ 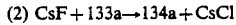

(3) $CsCl + nHF \rightarrow HCl + CsF \cdot nHF$ 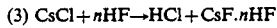

Equation (1) represents the first step of the process in which the molten composition is formed. Equation (2) represents the halogen exchange stage in which the HCFC-133a is passed through the molten composition to yield HFC-134a, which is removed as a gas and recovered as a liquid. Equation (3) represents the regeneration stage in which the CsF is reformed from CsCl and combined with additional HF to form the molten composition of $CsF \cdot nHF$.

The invention is applicable to the fluorination of saturated halocarbons having one or more replaceable halogens other than fluorine. The term "saturated" used herein is meant to include halocarbons wherein the halogen to be replaced by fluorine is bonded to a saturated, that is, sp3 hybridized carbon atom that, in turn, is bonded only to hydrogen, halogen, or another sp3 hybridized carbon atom. In other words, any constituent containing carbon-carbon unsaturation, if present, will be at least two carbon atoms removed from the carbon atom bearing the halogen to be replaced.

The saturated halocarbons can be composed of carbon and halogen or of carbon, hydrogen and halogen, where halogen stands for fluorine, chlorine, bromine, or iodine, with at least one of the halogen atoms being other than fluorine. Preferably, the halogen atoms other-than-fluorine will be chlorine or bromine; more preferably, chlorine because of the greater availability and broader utility of compounds containing chlorine. Included are perhalocarbons, composed of carbon and halogen, and halohydrocarbons composed of carbon, hydrogen, and halogen. The hydrogen-containing halocarbons are preferred because of the low ozone depletion potentials of their fluorinated derivatives. Overall, the halocarbons will normally contain 1 to 6 carbon atoms, preferably at least 2 carbons, more preferably 2 to 3 carbons, most preferably 2 carbon atoms because of their greater commercial importance. They will have normal boiling points in the range of −8° C. to 130° C., more usually −40° to 120° C. Included are alicyclic as well as acyclic compounds.

The fluorinated hydrocarbon products that may be prepared by the invented process can comprise carbon and halogen or carbon, hydrogen and halogen, with at least one halogen being a fluorine atom. Included are unsaturated as well as saturated fluorinated hydrocarbons, as illustrated in the accompanying table and examples. Preferred products contain hydrogen in addition to fluorine, with chlorine optionally present.

One of the advantages of the invented process over those disclosed previously lies in the structure of the fluorinated product. It has been found that the structure of the other-than-fluoride halide-containing saturated halocarbon is largely preserved after fluorination in the fluorinated hydrocarbon product without rearrangement to undesirable isomers. In prior art processes, the product tends to rearrange to form the thermodynamically most stable product. Thus, HCFC-133 tends to yield HFC-134a, instead of the desired HFC-134, in the processes of the prior art.

Representative fluorinatable halocarbons and fluorinated hydrocarbons that can be produced therefrom in accordance with the process of the invention are listed in the following table. It should be understood that the compounds listed in the table are not all inclusive; and that one skilled int he art may use the invention to form additional fluorinated hydrocarbons from other fluorinatable hydrocarbons.

| Halocarbon Reactants | | Fluorinated Hydrocarbon Products | |
|---|---|---|---|
| $CHCl_3$ | $CCl_4$ | $CHCl_2F$ | $CCl_2FCH_2Cl$ |
| $CHCl_2F$ | $CCl_3F$ | $CHClF_2$ | $CClF_2CH_2Cl$ |
| $CHClF_2$ | $CCl_2F_2$ | $CHF_3$ | $CF_3CH_2Cl$ |
| $CH_3CH_2Br$ | $CH_3CCl_3$ | $CClF_3$ | $CF_3CH_2F$ |
| $CH_2ClCH_2Cl$ | $CH_3CCl_2F$ | $CCl_2F_2$ | |
| $CH_2ClCH_2F$ | $CH_3ClF_2$ | $CClF_3$ | $CHClFCHCl_2$ |
| $CH_3CHCl_2$ | $CHCl_2CHCl_2$ | $CH_3CH_2F$ | $CHF_2CHCl_2$ |
| $CH_3CHClF$ | $CHClFCHCl_2$ | $CH_2ClCH_2F$ | $CHF_2CHClF$ |

-continued

| Halocarbon Reactants | | Fluorinated Hydrocarbon Products | |
|---|---|---|---|
| $CCl_3CH_2Cl$ | $CHF_2CHCl_2$ | $CH_2FCH_2F$ | $CHF_2CHF_2$ |
| $CCl_2FCH_2Cl$ | $CHF_2CHClF$ | $CH_3CHClF$ | $CF_3CH_2CH_2F$ |
| $C_3CFBrCF_2CF_3$ | | | |
| $CF_3CH_2CH_2Cl$ | $CHClFCCl_3$ | $CClF_2CHCl_2$ | $CF_3CF_2CF_3$ |
| $CF_3CF_2CH_2Cl$ | $CHClFCCl_2F$ | $CF_3CHCl_2$ | $CF_3CF_2CF_2CF_3$ |
| $CF_3CFBrCF_2Br$ | $CHF_2CCl_3$ | $CF_3CHClF$ | $CF_2ClCH_2F$ |
| $CF_3CF_2CFBrCF_2Br$ | | $CHF_2CClF_2$ | $CH_3CF_2Cl$ |
| $CF_3CHCl_2$ | $CHClFCClF_2$ | $CF_3CHF_2$ | $CHClFCH_2F$ |
| $CHF_2CCl_2F$ | $CHF_2CClF_2$ | $CHF_2CH_2Cl$ | $CHF_2CH_2F$ |
| $CH_2CCl_3$ | $CHFClCHFCl$ | $CF_3CF_2CHF_2$ | $CF_3CF_2CHClF$ |
| $CCFCl_2CH_2F$ | $CClF_2CH_2F$ | $CF_3CF_2CHCl_2$ | $CF_3CHFCF_3$ |
| $CHCl_2CH_2Cl$ | $CHClFCH_2Cl$ | $CF_3CHFCF_2Cl$ | $CF_3CHFCFCl_2$ |
| $CHCl_2CH_2F$ | $CHF_2CH_2Cl$ | $CF_3CH_2CF_3$ | |
| $CF_2ClCH_2CF_2Cl$ | | | |
| $CHFClCH_2F$ | $CH_3CH_2Cl$ | $CF_3CH_2CF_2Cl$ | |
| $CFCl_2CCl_2CHCl_2$ | | | |
| $CCl_3CCl_2CHCl_2$ | $CF_3CF_2CHCl_2$ | $CF_2ClCCl_2CHCl_2$ | $CF_3CCl_2CHCl_2$ |
| $CF_3CCl_2CHCl_2$ | | | |
| $CFCl_2CCl_2CHCl_2$ | $CF_2ClCCl_2CHCl_2$ | $CF_3CClFCHCl_2$ | |
| $CF_3CCl_2CHCl_2$ | $CF_3CClFCHCl_2$ | | |
| $CF_3CF_2CHFCl$ | $CCl_3CClFCHCl_2$ | | |
| $CCl_3CF_2CHCl_2$ | $CCl_3CF_2CHClF$ | | |
| $CCl_3CF_2CHF_2$ | $CCl_3CCl_2CHFCl$ | | |
| $CCl_3CCl_2CHF_2$ | $CF_3CH_2CF_2Cl$ | | |
| $CF_2ClCH_2CF_2Cl$ | $CFCl_2CH_2CF_2Cl$ | | |
| $CFCl_2CH_2CFCl_2$ | $CCl_3CH_2CFCl_2$ | | |
| $CCl_3CH_2CCl_3$ | | | |

The molten compositions are basically well-known alkali metal acid fluoride compositions. They are readily prepared by reaction of an alkali metal chloride or fluoride with hydrogen fluoride. When molten, they exist largely as alkali metal cations, $M^+$, and acid fluoride anions, $[H_nF_{n+1}]^-$, where "n" is a number of at least 0.5, depending on the number of molecules of HF associated with the fluoride ion. It is convenient, however, to represent them as MF.nHF, where "M" represents the alkali metal and "n" is as above. For the purposes of this invention, "n" will normally not be greater than about 2, preferably not greater than about 1.5, more preferably not greater than 1. It will be appreciated that when n=1, the acid fluoride is a hydrogen difluoride, commonly referred to as a "bifluoride"; when n=2, the acid fluoride is a dihydrogen trifluoride; and when n=1.5 the acid fluoride is a mixture of bifluoride and dihydrogen trifluoride. When an additive such as 50 mole % of MF is used along with 50 mole % of the bifluoride, then n=0.5.

In general, the higher the value of "n", the lower the melting point of the alkali metal acid fluoride, as illustrated in the table below. The table lists melting points of the Cs and Rb acid fluorides as a function of "n" (HF content). Variations in the melting point for the same acid fluoride may be attributed to deviations from stoichiometry or trace impurities, e.g. water in the fluorides, etc. or to the determination method employed. The melting point decreases with an increase in the value of "n" and with an increase in the atomic weight of the alkali metal from Rb to Cs.

TABLE A

| Melting Points (°C.) of Alkali Metal Fluorides and Bifluorides | | | |
|---|---|---|---|
| | Dihydrogentrifluoride | n=1 | |
| Metal | Fluoride[1] (°C.) | Bifluoride (°C.) | n=2 (°C.) |
| Rb | 760 | 204[2], 210[3] | approx 52 |
| Cs | 683 | 205[4], 180[3], 176[4] | approx 150 |

[1]Lange's Handbook of Chemistry - 10th ed., McGraw Hill, 1961.
[2]Chaudhuri et al., Chem. Ind. (London), 88 (1979).
[3]Westrum et al., J. Chem. Thermodynamics 10, 835 (1979).
[4]Winsor et al., J. A. Chem. Soc. 70 1500 (1948).

The alkali metal acid fluorides of Rb or Cs may be used singly or as mixtures with one another, also, singly or as mixtures with up to 50 mole percent of another alkali metal acid fluoride or chloride, e.g., lithium, sodium or potassium acid fluorides or acid chlorides or one or more alkali metal fluorides and/or other alkali metal halides, e.g. chlorides. The bifluorides of Rb and/or Cs, singly or in admixture, are preferred, because of their low melting points, in particular the cesium compound. Lithium, sodium and/or potassium fluorides or chlorides, preferably fluorides, may be employed in minor amounts mixed with the rubidium and/or cesium bifluorides. Less preferred but useful are minor amounts of the fluorides or chlorides of Ca, Sr, Ba, B, Al or La. Even less preferred but still useful are minor amounts of the fluorides or chlorides of Ti, Zr, Hf, V, Nb, Ta, Cr, Mo, Fe, Co, Ni, Cu, Zn, Ag, Mn, Hg, Cd, Sn, Pb, and Sb.

Molten salt compositions containing up to 50 mole % alkali metal fluoride along with the bifluoride constitute a preferred aspect of the invention. It is believed that such compositions contain free fluoride ion. Any of the alkali metal fluorides may be used as the "free" fluoride ion source in mixtures with any one or both of the Cs or Rb bifluorides provided the bifluoride-fluoride mixtures are molten at the desired fluorinating temperature. The "free" fluoride content is generally in the range of about 0.05 to 1 mole per mole of bifluoride, preferably 0.1 to 0.5. Cesium bifluoride and cesium fluoride, for example, form a eutectic consisting of about 54 mole % bifluoride and 46 mole % fluoride melting at about 152° C. Practically speaking, the existence of "free" fluoride in mixed acid fluoride-fluoride salts depends upon the presence of bifluoride since any higher acid fluoride will consume fluoride.

Specific embodiments of this invention are illustrated in the examples which follows, Example 15 being the best mode contemplated for performing the invention.

The examples were conducted in a 600 ml autoclave composed of stainless steel, "Inconel" alloy or "Hastelloy" The autoclave was equipped with a gas feed tube, an outlet tube, a stirrer, a heating mantle controlled by a thermocouple centered within the reactor and a pressure transducer for monitoring pressure within the autoclave. The outlet tube was connected is series with a primary gas scrubber containing aqueous caustic, a similarly constituted back-up scrubber, and a gas chromatograph (GC) adapted to automatically sample and analyze gaseous effluent from the reactor. In some examples, the GC results were confirmed with a mass spectrometer (MS). All reactants employed were anhydrous. The gas chromatograph (GC) was a "Hewlett Packard" 5880 model utilizing a flame ionization detector and a customized 4-component column. Analyses of the scrubber solution(s) were carried out using fluoride and chloride specific ion electrodes.

EXAMPLE 1

To the 600 cc stainless steel Parr autoclave was added 900 gm (5.92 mole) cesium fluoride and 108 gm (5.40 mole or 0.9 equivalents) HF. The reactor contents approximated CsF.0.9 HF. The reactor was heated to 300° C. Melting of the reactor contents was noted at ca. 200° C. by hand-turning the stirrer shaft. Thereafter, vigorous agitation was provided by mechanical means. Gaseous HCFC-133a was then passed at atmos. pressure, through the molten composition at a rate of 160 ml/minute at 300° C. Conversion to reaction products of HCFC-133a rose steadily to ca. 14% with 98% selectivity to HCFC-134a over a reaction period of 4.25 hours.

EXAMPLE 2

To the 600 cc Parr stainless steel autoclave was added 900 gm (5.92 mole) cesium fluoride and 108 gm (5.40 mole or 0.9 equivalent) HF. The reactor was heated to 300° C., and gaseous HCFC-133a was passed into the vigorously agitated molten fluoride at a rate of 70 ml/minute. Gaseous HF was fed to the reactor at the same time, at a rate of 4000 ml/minute, resulting in ca. 4.02 moles additional HF added during the first hour of operation. Thus, the total amount of HF added to the reactor over the first hour corresponded to about 1.6 moles per initial mole of CsF. The HF:HCFC-133a feed ratio was varied between 1:1 and 1:4 over the next 90 hours and the effect on conversion to fluorinated products determined.

During the first 20 hours with a feed ratio of 1:1, the conversion rose steadily to 3%. The HF feed was then reduced to 1:2 and maintained for a second 20 hour period. Conversion during this period rose to 4%. The HF feed rate was then further reduced to 1:4 and this was maintained for the next 50 hours. Conversion during this time rose to 7%. Selectivity to HFC-134a was greater than 90% over the entire run.

EXAMPLE 3

A 600 cc stainless steel Parr autoclave fitted with "Hastelloy" C impellors and stirrer shaft and an Inconel 600 dip leg, was charged with 607.6 g (4 mole) CsF and 58.1 (1 mole) KF. The reactor was evacuated to ca. 100 torr pressure and 80 g (4 moles) HF was added. Reactor contents approximated 5 moles of alkali metal ions, 4 moles of bifluoride ion (FHF−) and 1 mole of fluoride ion (F−) or 0.8 Cs+K+ +0.8HF2− +0.2F−. This system was then heated to 300° C. and HCFC-133a admitted at a constant rate of 11.1 ml/minute to the agitated molten mixture.

The reactor effluent was sampled automatically and analyzed by gas chromatograph. The conversion during the first 1.5 hours was 100%; dropped to about 70% over the next hour; and continued at this rate for 7.5 hours with selectivity to HFC-134a being greater than 96% over the complete run. $CHCl=CF_2$ (HCFC-1122) is also formed by the elimination of HF from HCFC-133a and constituted the remaining less than 4%.

EXAMPLE 4

A 600 cc "Hastelloy" C Parr autoclave was charged with 848 gms (5.58 mole) CsF, 85 gms (1.46 mole) KF and 112 gms (5.60 mole) HF. The resulting mixture, consisting essentially of Cs and K cations and bifluoride and fluoride anions, was heated to 300° C. and HCFC-133a vapor was passed through the molten mixture at a constant rate of approximately 100 ml/minute. HF vapor was simultaneously fed through the mixture, initially at a rate of 5 ml/minute, which corresponded to a HF:HCFC-133a ratio of 1:20. The HF feed rate was increased stepwise, eventually to 30 ml/minute (HF:HCFC-133a ratio =3:10) during a total run time of 100 hours. The HF:HCFC-133a feed ratio was held at 1:20 for the first 28 hours. During this period, conversion to reaction products rose quickly to, and levelled out at 20% with greater than 95% selectivity to HFC-134a.

The HF:HCFC-133a feed ratio was then changed to 1:10 for the next 4.5 hours and the conversion increased to 25%, with greater than 99% selectivity to HFC-134a. The HF:HCFC-133a feed ratio was again decreased to 1:20 whereupon the conversion to reaction product of HCFC-133a dropped steadily in 20 hours to 5% indicating a decrease in available fluoride ion in the molten composition.

Increasing the HF feed to an HF:HCFC-133a ratio of 1:10 resulted in an increase in conversion to reaction products over the next 18 hours to 13%. At this point, the HCFC-133a feed line showed evidence of plugging and conversion dropped to 3%. After the feed was resumed at a HF:HCFC-133a feed ratio of 1:5, the conversion to fluorinated products recovered to 17% after 10 hours.

EXAMPLE 5

To a 600 cc stirrer-equipped 600 cc "Inconel" Parr autoclave was added 850 gms (5.6 mole) CsF, 41.8 gms (0.56 mole) KCl and 112 gms (5.60 mole) HF. The reactor contents were approximated by the molar ratios CsF.HF +0.1 KCl. The reactor mass was heated under agitation to 250° C., and gaseous HCFC-133a was fed through the molten salt mixture at an initial rate of 50 ml/minute. Gaseous HF was simultaneously fed to the reactor at a HF:HCFC-133a ratio of 1:2 and this ratio was maintained for 40 hours. During this time the conversion was about 1%. Analyses of the scrubber solution indicated that substantially all the chloride content had been removed as HCl, that very little of the HF fed was leaving the reactor, and that the reactor mass approached the molar composition CsF.1.9 HF.

Reducing the HF feed to a HF:HCFC-133a ratio of 1:7 resulted in a gradual rise in the conversion of HCFC-133a to its reaction products to 1.3% after 10 hours, as the amount of excess HF in the reactor was reduced. Decreasing the HF:HCFC-133a ratio to 1:20 and increasing the temperature to 300° C. resulted in a decrease in the HF content of the reaction mixture and a further increase in the conversion to 8%, with greater than 97% selectivity to HFC-134a.

The HF feed rate was then adjusted to match the HF consumption rate with the HF:HCFC-133a ratio varying from 1:6 to 1:13. Conversion of HCFC-133a was ca. 13% with selectivities greater than 98% to HFC-134a, observed when the run was terminated after 211 hours of operation.

EXAMPLE 6

This example illustrates batchwise production of HFC-134a in essentially quantitative conversion and yield.

To a 600 cc "Hastelloy" C Parr autoclave was added 805.0 gm (5.3 moles) CsF, and after evacuating to ca. 100 torr, 106.0 gm (5.3 moles) HF was added. Pot composition approximated CsF.1HF. The reactor was then warmed to HCFC-133a 200° C. while the pressure was monitored. At 200° C., 55.6 gms (0.53 mole) HCFC-133a was added and the reactor warmed to 200° C., 250° C. and 300° C., allowing for pressure equilibration, and the pressure and temperature recorded. Gas samples were taken for GC analysis at the three temperatures for conversion and selectivity to HFC-134a; and the results are shown in Table B.

TABLE B

| Time (hrs) | Temp., °C. | Press. psig | Sample # | % Conversion of HCFC-133a | Selectivity to HFC-134a |
|---|---|---|---|---|---|
| 2.00 | 198 | 405 | 1 | 10.0 | 96.7 |
| 3.75 | 251 | 402 | 2 | 48.2 | 98.6 |
| 6.30 | 300 | 463 | 3 | 94.7 | 98.9 |
| 21.00 | 199 | 288 | 4 | 98.1 | 98.9 |

EXAMPLE 7

To a "Hastelloy" C Parr autoclave (600 cc) was added 759.5 gm (5.0 mole) CsF and 90 gm (4.5 mole) HF. Pot composition approximated CsF:0.9HF. Then $CCl_2FCH_2Cl$, i.e., HCFC-131a was pumped to the reactor at a rate of ca. 1.3 gms/minute. The reactor mass was sampled constantly by passing the reactor effluent through a caustic scrubber and then a gas bulb. Thus, both liquid and gas samples were taken simultaneously. The reactor temperature, initially at 150° C., was raised after 25 minutes to 200° C. and then, after an additional 25 minutes, to 250° C. Eleven liquid samples and ten gas samples were collected over the 61 minutes run time. Fifty-three percent of the feed was recovered as liquid samples, the remainder as non-condensed gas samples. The liquid samples consisted primarily of unreacted $CCl_2FCH_2Cl$ and $CHCl=CClF$ (via loss of HCl from $CCl_2FCH_2Cl$). The gas samples consisted predominantly of $CHCl=CClF$, $CF_3CH_2Cl$ (HFC-133a), $CHCl=CF_2$ (via loss of HCl from $CF_3CH_2Cl$), $CClF_2CH_2Cl$ and $CF_3CH_2F$ (HFC-134a).

EXAMPLE 8

To a "Hastelloy" C Parr autoclave (600 cc) was added 607.6 gm (4.0 mole) CsF and 180 gm (8.0 mole) HF. Pot composition approximated CsF·2HF. The autoclave was sealed and cooled to 70° C. and 38.0 gms (0.25 mole) $CCl_2FCH_2Cl$ (HCFC-131a) was added in one portion. The reactor was allowed to warm to room temperature and then heated to 40° C. Samples were taken periodically and analyzed by GC or GC/MS. The reactor temperature was varied between 40° C. and 150° C. over the 27 hour run time.

Gas samples were taken at various times from 0.48 and 25.30 hours and at various temperatures, noted in Table C below, and analyzed. The results follow:

TABLE C

| Sample | Time | Temp., °C. | CClF=CHCl | $CClF_2CH_2Cl$ $CClf_2CH_2Cl$ | (CHFC-133a) $CF_3CH_2Cl$ | (HFC-134a) $CF_3CH_2F$ |
|---|---|---|---|---|---|---|
| 1 | 0.48 | 78 | 0.07% | 0.43% | 1.91% | 0.20% |
| 2 | 0.88 | 71 | 0.06% | 1.95% | 3.50% | 0.20% |
| 3 | 1.50 | 62 | 0.05% | 2.35% | 4.51% | 0.33% |
| 4 | 2.30 | 54 | 0.02% | 1.94% | 3.32% | 0.20% |
| 5 | 19.32 | 52 | 0.03% | 1.51% | 2.01% | 0.22% |
| 6 | 23.23 | 72 | 0.06% | 2.22% | 3.15% | 0.28% |
| 7 | 24.07 | 103 | 0.005% | 5.74% | 5.63% | 0.44% |
| 8 | 25.30 | 102 | 0.05% | 5.40% | 3.95% | 0.31% |

The extent of dehydrohalogenation observed in Example 7 was markedly reduced due to the higher HF to CsF mole ratio and the lower reaction temperatures employed herein.

EXAMPLE 9

To a "Hastelloy" C Parr autoclave (600 cc) was added 757.5 gm (5.0 mole) CsF and 99 gm (1 mole) $CH_2ClCH_2Cl$ (HCC-150). The autoclave was sealed, cooled to $-78°$ C. and evacuated to ca. 100 torr. Thereafter, 100.0 gms (5 mole) HF was added, and the reactor allowed to warm to room temperature and then heated to 200° C. Time, temperature and pressure were monitored and the reactor was sampled at T=61 minutes and T=140 minutes and at shutdown at T=180 minutes. These data are shown in Table D along with the composition of the samples taken:

TABLE D

| Time, min. | 61 | 140 | 180 |
|---|---|---|---|
| Temp., °C. | 190 | 191 | 192 |
| Press. psig | 517 | 418 | 394 |
|  | Sample 1 | Sample 2 | Sample 3* |
| $CH_2=CHF$ | 0.2% | 2.0% | 1.5% |
| $CH_2=CHCl$ | 1.9% | 41.0% | 3.4% |
| $CH_2FCH_2F$ (HFC-152) | 92.5% | 42.1% | 92.6% |
| $CH_2FCH_2Cl$ (HFC-151) | 4.7% | 8.5% | 2.3% |
| $CH_2ClCH_2Cl$ (HCC-150) | 0.8% | 0.1% | 0.0% |

*liquid sample taken after reactor was cooled to room temperature and shut down.

EXAMPLE 10

To a 600 cc Parr autoclave was added 757.5 gms (5 mole) CsF. The reactor was evacutated to vacuum and, then 100 gm (5 mole) HF was added. The reactor was cooled to below room temperature. To the reactor was then added 99 gms (1 mole) $CH_2ClCH_2Cl$ (HCC-150) in one portion and the system pressured to 300 psig with dry nitrogen. The reactor was then warmed to 200° C. with a back pressure regulator set at 300 psig. Samples were collected continuously as the pressure greater than 300 psig was vented by the back pressure regulator. The back pressure was reduced in steps to maintain sample collection. The samples were analyzed by GC and confirmed by GC/MS. Total run time was 15.5 hours.

TABLE E

| Sample # | Time (hrs) | Temp. (°C.) | Pressure (psig) | $CH_2=$ CHF % | $CH_2FCH_2F$ % | $CH_2=$ CHCl % | $CH_2FCH_2Cl$ % |
|---|---|---|---|---|---|---|---|
| 1 | 4.00 | 202 | 293 | 0.00 | 15.35 | 61.64 | 2.30 |
| 2 | 5.72 | 200 | 173 | 0.18 | 50.93 | 35.01 | 4.77 |
| 3 | 7.57 | 202 | 177 | 0.08 | 61.12 | 15.79 | 9.63 |
| 4 | 8.47 | 201 | 90 | 0.54 | 55.71 | 9.96 | 14.98 |
| 5 | 8.95 | 202 | 37 | 0.00 | 54.14 | 20.07 | 12.12 |
| 6 | 13.42 | 202 | 0 | 0.00 | 69.14 | 9.44 | 15.07 |

EXAMPLE 11

This example illustrates the preparation of $CHF_2CHF_2$ (HCFC-134) as well as $CF_3CH_2F$ (HCFC-134a), $CHClFCHF_2$ (HCFC-133) $CF_3CH_2Cl$ (HCFC-133a) and various fluoroolefins.

To a 600 cc Parr autoclave was added 759.5gms (5 mole) CsF. The reactor was evacuated to vacuum and then 100 gms (5 mole) HF was added. The reactor temperature was cooled to below room temperature and 67.76 gms (0.5 mole) $CHF_2CHCl_2$ (HCFC-132a) was added. The reactor was then heated to 204° C. in 42 minutes and held for a total of 156 minutes. Six samples were taken periodically as noted in Table E below by venting the reactor through a heated line into a 5% KOH scrubber, then through a gas bulb followed by a dry test meter. These were analyzed by GC and confirmed by GC/MS. Mass balance was 86%. Results follow:

TABLE F

| | Sample # | | | | | |
|---|---|---|---|---|---|---|
| | 1 | 2 | 3 | 4 | 5 | 6 |
| Time Min. | 52 | 63 | 70 | 78 | 148 | 156 |
| Press. psig | 320 | 344 | 315 | 285 | 108 | 0 |
| Products | | | | | | |
| $CF_3CH_2F$ | 22.9 | 22.2 | 22.4 | 22.3 | 20.1 | 21.9 |
| $CHF_2CHF_2$ | 10.2 | 12.0 | 12.1 | 11.7 | 9.4 | 9.4 |
| $CF_3CH_2Cl$ | 22.8 | 26.8 | 26.9 | 26.4 | 27.9 | 23.3 |
| $CHClCHF_2$ | 1.2 | 2.2 | 2.2 | 2.2 | 2.2 | 1.5 |
| $CHF=CF_2$ | .2 | .2 | .2 | .2 | .1 | .1 |
| $CHCl=CF_2$ | 4.1 | 5.4 | 5.1 | 4.8 | 3.4 | 2.5 |
| $CHF=CClF$ | 2.3 | 3.7 | 3.5 | 3.4 | 2.5 | 1.7 |
| $CHF=CCl_2$ | 6.5 | 10.2 | 11.0 | 11.3 | 14.3 | 13.4 |
| $CHF_2CHCl_2$ | 29.6 | 7.1 | 16.4 | 17.5 | 19.7 | 26.7 |

EXAMPLE 12

This example illustrates the preparation of fluorinated derivatives of chloroform.

To a 600 cc Parr autoclave was added 607.6 gms (4 mole) CsF. The reactor was sealed and evacuated, and then 72 gm (3.6 mole) HF was added in one portion. Pot composition approximated CsF·0.9HF. The reactor was then warmed to 250° C. with a back pressure regulator set at 300 psig. To the reactor was then added 73.5 gms (0.615 mole) chloroform (by inverting a pressurized cylinder and blowing the organic compound into the reactor) in one portion. Gas samples were collected continuously as the pressure above 300 psig was vented by the back pressure regulator. The back pressure was reduced in steps to maintain sample collection. The samples were analyzed by GC, confirmed by GC/MS. After 25 minutes of reaction time the conversion of $CHCl_3$ to $CHF_3$ was 97%, to $CHClF_2$ 3%. After 180 minutes, the conversion to $CHF_3$ was 99%, to $CHClF_2$ 1%. After 202 minutes, the conversion to $CHF_3$ was 100%. Repeating the above process at 170° C. resulted in an overall conversion of $CHCl_3$ to fluorinated products of 7.3% after 199 minutes of reaction time. The major product was $CHF_3$ along with minor amounts of $CHCl_2F$ and $CHClF_2$.

EXAMPLE 13

This example illustrates the conversion of $CCl_4$ to fluorinated derivatives.

To a 600 cc Parr autoclave was added 759.5 gms (5 mole) CsF and 77.0 gms (0.5 mole) carbon tetrachloride. The reactor was cooled to ca. −78° C. and evacuated to vacuum. Then 100 gms (5 mole) HF was added and the reactor temperature increased to 200° C. while monitoring the temperature and pressure. Four initial samples were taken by venting the reactor through a heated line into a 5% KOH scrubber, then a gas bulb followed by a dry test meter, under the following conditions of time, temperature and pressure: (1) after 180 minutes at 200° C. and 222 psig, (2) 222 minutes at 205° C. and 218 psig, (3) 262 minutes at 205° C. and 60 psig and (4) 291 minutes at 200° C. and 0 psig.

The samples were analyzed by GC and confirmed by GC/MS. Mass balance was 93%. Overall conversion of $CCl_4$ to products was 1.4%. Products were $CCl_3F$, $CCl_2F_2$, $CClF_3$ and $CF_4$.

EXAMPLE 14

To a 600 cc Parr autoclave was added 607.6 gms (4 mole) CsF. The reactor was sealed and evacuated, then 72 gms (3.6 mole) HF was added in one portion. Pot composition approximated CsF·0.9HF. The reactor was then warmed to 250° C. with a back pressure regulator set at 300 psig. To the reactor was then added 73.5 gms (0.615 mole) chloroform (by inverting a pressurized cylinder and blowing the organic compound into the reactor) in one portion. Gas samples were collected continuously as pressure less than 300 psig was vented by the back pressure regulator. The back pressure was reduced in steps to maintain sample collection. The samples were analyzed by GC and confirmed by GC/MS. Total run time was 5.3 hours. No mass balance was obtained.

TABLE G

| Sample | Time (min) | Temp. (°C.) | CHF₃ % | CHClF₂ % | CHCl₂F % | CHCl₃ % |
|---|---|---|---|---|---|---|
| 1 | 25 | 250 | 96.97 | 3.03 | 0.00 | 0.00 |
| 2 | 128 | 250 | 96.95 | 3.05 | 0.00 | 0.00 |
| 3 | 163 | 250 | 93.46 | 1.23 | 5.31 | 0.00 |
| 4 | 168 | 250 | 98.89 | 1.11 | 0.00 | 0.00 |
| 5 | 180 | 250 | 99.03 | 0.97 | 0.00 | 0.00 |
| 6 | 200 | 250 | 98.96 | 1.04 | 0.00 | 0.00 |
| 7 | 240 | 250 | 98.68 | 1.32 | 0.00 | 0.00 |
| 8 | 292 | 250 | 100.00 | 0.00 | 0.00 | 0.00 |

EXAMPLE 15

To a 600 cc "Hastelloy" C Parr autoclave was added 607.6 gm (4 mole) CsF, 58.1 gm (1 mole) KF and 80 gm (4 mole) HF. The reactor was then warmed to 300° C. with a back pressure regulator set at 300 psig. Liquid HCFC-133a was then continuously fed to the agitated molten mixture at a constant rate of 0.0192 mole per minute by means of a high pressure liquid chromatography (HPLC) pump. Gas samples were then collected continuously as pressure greater than 300 psig was vented by the back pressure regulator. The reactor effluent was sampled automatically and analyzed by gas chromatography (GC). The conversion during the first 1.2 hours was 59%; dropping slowly to 27% over the next 1.2 hours. Selectivity to HFC-134a was greater than 99% over the entire run. HCFC-1122 is also formed by elimination of HF from HCFC-133a and constituted the remaining less than 1%.

EXAMPLE 16

To a 600 cc "Hastelloy" C Parr autoclave was added 607.6 gm (4 mole) CsF, 58.1 gm (1 mole) KF and 80 gm (4 mol) HF. The reactor was then warmed to 300° C. with a back pressure regulator set at 450 psig. Liquid HCFC-133a was then continuously fed to the agitated molten mixture at a constant rate of 0.041 mole per minute by means of an HPLC pump. Gas samples were then collected continuously as pressure greater than 450 psig was vented by the back pressure regulator. The reactor effluent was sampled automatically and analyzed by GC. The conversion during the first 0.7 hours was 52%; dropping slowly to 18.8% over the next 0.8 hours. Selectivity to HFC-134a was greater than 99% over the entire run. HCFC-1122 is also formed and constituted the remaining less than 1%.

EXAMPLE 17

To a 600 cc "Hastelloy" C Parr autoclave was added 607.6 gm (4 mole) CsF, 58.1 gm (1 mole) KF and 80 gm (4 mole) HF. The reactor was then warmed to 300° C. with a back pressure regulator set at 600 psig. Liquid HCFC-133a was then continuously fed to the agitated molten mixture at a constant rate of 0.041 mole per minute by means of an HPLC pump. Gas samples were then collected continuously as pressure greater than 600 psig was vented by the back pressure regulator. The reactor effluent was sampled automatically and analyzed by GC. The conversion during the first 0.65 hours was 58%; dropping slowly to 40% over the next 0.27 hours. Selectivity to HFC-134a was greater than 99% over the entire run. HCFC-1122 is also formed and constituted the remaining less than 1%.

We claim:

1. A process for the halogen exchange fluorination of a saturated halocarbon having at least one replaceable halogen other than fluorine to a fluorinated hydrocarbon having at lest one more fluorine in the molecule than the saturated halocarbon which comprises the following steps: (1) intimately contacting the saturated halocarbon with an anhydrous molten composition containing at least 50 mole % of a compound or compounds having the formula MF.nHF wherein "M" is at least one of cesium or rubidium, HF is hydrogen fluoride and "n" is a number from about 0.5 to 3, at a temperature within the range of about 30° C. up to a temperature below the decomposition temperature of said halocarbon or said fluorinated hydrocarbon, whichever is lower, at a pressure and for a time sufficient to yield at least one reaction product or said fluorinated hydrocarbon having at least one more fluorine in the molecule than said saturated halocarbon and a residual molten composition at least partially depleted in its fluoride content and enriched in its other-than-fluoride halide content; (2) isolating and recovering the fluorinated reaction product from the residual molten composition.

2. A process as in claim 1 wherein "M" is cesium.

3. A process as in claim 2 wherein "n" is 0.5.

4. A process as in claim 1 wherein said saturated halocarbon is 2-chloro-1,1,1-trifluorethane, and said fluorinated hydrocarbon is 1,1,1,2-tetrafluoroethane.

5. A process as in claim 1 wherein said saturated halocarbon is 1,2-dichloroethane, and said fluorinated hydrocarbon is 1,2-difluoroethane.

6. A process as in claim 1 wherein said saturated halocarbon is 2-chloro-1,1,1-trifluoroethane, chloroform, carbon tetrachloride, 1,1-dichloro-2,2-difluoroethane, 1-fluoro-1,1,2-trichloroethane, 2,2-dichloro-1,1,1-trifluoroethane, 1,2-dichloroethane or 1,2-dichloro-1-fluoroethane.

7. A process as in claim 1 wherein said saturated halocarbon is 1,1-dichloro-2,2-difluoroethane and said fluorinated product is 1,1,2,2-tetrafluoroethane.

8. A process as in claim 1 wherein "n" is a number from about 0.5 to 1.

9. A process as in claim 1 wherein said temperature is about 200° C. to about 350° C.

10. A process as in claim 1 wherein said pressure is about atmospheric pressure (14.7 psi) to about 1500 psi.

11. A process as in claim 1 wherein said contacting step involves a period of 0.5 minute to about 120 minutes.

12. The process of claim 1 wherein said residual molten composition is treated with hydrogen fluoride to obtain an anhydrous molten composition containing a substantial amount of MF.nHF in said molten composition and HX wherein X is the halide that is other than fluoride.

13. A process for the fluorination of 2-chloro-1,1,1-trifluoroethane comprising (1) intimately contacting 2-chloro-1,1,1-trifluoroethane with molten CsF.nHF wherein "n" is a number from about 0.5 to 1 at a temperature of about 180° C. to about 350° C. to produce 1,1,1,2-tetrafluoroethane, (2) isolating said 1,1,1,2-tetrafluoroethane as a gas and cooling said gas to recover liquid 1,1,1,2-tetrafluoroethane.

14. A process as in claim 1 wherein HF and said halohydrocarbon are cofed continuously to contact said anhydrous molten composition to produce said fluorinated halohydrocarbon and hydrogen chloride while regenerating said molten composition.

* * * * *

UNITED STATES PATENT AND TRADEMARK OFFICE
CERTIFICATE OF CORRECTION

PATENT NO. : 4,900,702

DATED : February 13, 1990

INVENTOR(S) : Takashi Tsuboi and Hitoshi Ueda

It is certified that error appears in the above-identified patent and that said Letters Patent is hereby corrected as shown below:

Claim 3, column 6, line 25, change "$0 \leq e \leq 2$" to --$0 < e \leq 2$--.

Signed and Sealed this

Ninth Day of July, 1991

*Attest:*

HARRY F. MANBECK, JR.

*Attesting Officer*      *Commissioner of Patents and Trademarks*